United States Patent [19]

Hittman et al.

[11] 4,006,735
[45] Feb. 8, 1977

[54] PRESSURE SENSOR APPARATUS
[75] Inventors: Fred Hittman, Baltimore; Lewis Fleischmann, Randallstown, both of Md.
[73] Assignee: Hittman Corporation, Columbia, Md.
[22] Filed: July 16, 1974
[21] Appl. No.: 488,987
[52] U.S. Cl. .................................. 128/2 A; 73/406; 128/2.05 D; 128/2.05 E; 250/336
[51] Int. Cl.² .......................................... A61B 5/00
[58] Field of Search ......... 128/2 A, 2.05 D, 2.05 E, 128/350 R, 350 V, 1 R; 73/406, 393, 409, 410, 407; 250/336 R

[56] References Cited
UNITED STATES PATENTS

| | | | |
|---|---|---|---|
| 3,034,356 | 5/1962 | Bieganski et al. | 128/2.05 E |
| 3,503,402 | 3/1970 | Schulte | 128/350 V |
| 3,625,199 | 12/1971 | Summers | 128/2.05 E |
| 3,686,958 | 8/1972 | Porter et al. | 73/406 |
| 3,789,667 | 2/1974 | Porter et al. | 73/406 |

*Primary Examiner*—Kyle L. Howell
*Attorney, Agent, or Firm*—Fleit & Jacobson

[57] ABSTRACT

A pressure sensor apparatus primarily for sensing pressure in a body cavity such as the cranium, bladder or vena cava of an animal or human comprising a housing having non-radioactive fluids contained in two spaced apart regions of the housing. A radioactive fluid immiscible with at least one of the non-radioactive fluids is also contained within the housing between the non-radioactive fluids. The interface between the radioactive fluid and one of the non-radioactive fluids is optionally formed by a resilient member such as an elastomeric diaphragm. A flexible member is connected to the housing and communicates with one of the two spaced apart regions in the housing. The other spaced apart region in the housing is closed by a resilient member such as a metallic diaphragm. With this arrangement, the movement of the radioactive fluid is proportional to the pressure sensed by the flexible member and is sensed by a radiation detector.

9 Claims, 5 Drawing Figures

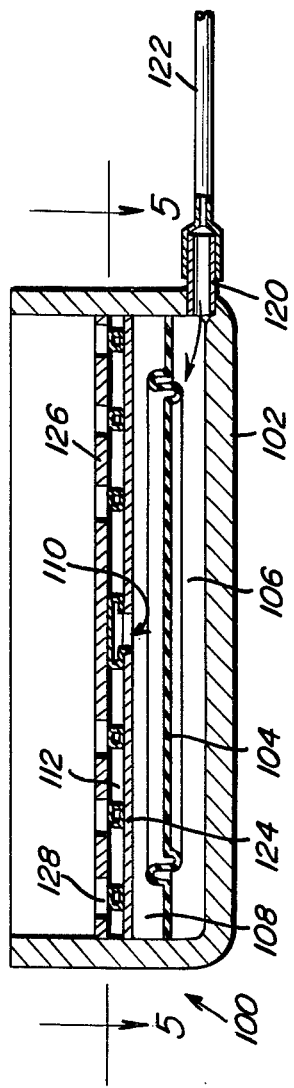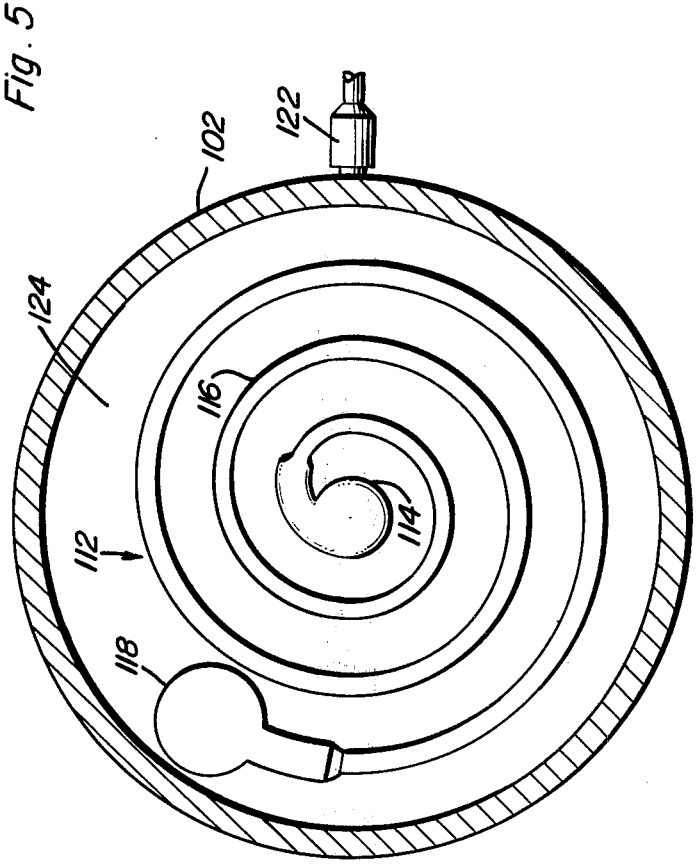

PRESSURE SENSOR APPARATUS

CROSS-REFERENCE TO RELATED APPLICATION

This application is related to commonly assigned application Ser. No. 478,763, filed June 12, 1974, for Pressure Sensor Apparatus, by Thomas S. Bustard et al, now abandoned.

BACKGROUND OF THE INVENTION

The need for a non-invasive technique for measuring the pressure in body cavities of animals or humans is recognized as highly desirable for continuous or intermittent monitoring of body conditions. Such cavities as the cranium, vena cava, bladder, and others provide valuable and sometimes critical information for maintaining the well being or survival of an animal or human. For example, it is known that intercranial pressure provides a valuable indication of well being for a variety of clinical conditions.

A long-term, non-invasive monitor of intracranial pressure is particularly desirable for the congenital hydrocephalic. This condition is one in which the normal production of cerebral spinal fluid is not balanced by reabsorption of the fluid. The retained fluid increases the intracranial pressure and causes head swelling which is a characteristic of hydrocephalus. The increase in intracranial pressure can eventually lead to disability or death.

The normal treatment for hydrocephalus comprises surgically implanting a fluid shunt to transfer cerebrospinal fluid from the intracranial cavity to other parts of the body such as the peritoneal cavity or the jugular vein. The surgically implanted shunt is basically a drainage tube which contains a check valve and requires a modest pressure differential for the cerebrospinal fluid to flow. These shunts often become partially or even fully blocked and intracranial pressure starts to rise resulting in intracranial hypertension.

The symptoms characteristic of a blocked shunt are also characteristic of various other maladies. Early symptoms of a clogged shunt are nausea, headache, and dizziness, any of which can result from many other causes other than intracranial hypertension. In young children especially a physician cannot easily determine shunt blockage without performing a surgical procedure. The presence of an indwelling pressure sensor would permit the physician to directly monitor the intracranial pressure and remove a substantial amount of the risk from his diagnosis.

An additional problem associated with a blocked vent is the rate at which the pressure can rise. Drastic increases can occur within less than an hour. Since a high pressure that is maintained for a period of time will cause irreversible brain damage, it is imperative that pressure increases be discovered in the shortest possible time. Full utilization of a pressure sensor requires a simplified determination of the pressure so that even a parent can perform the determination.

Against this background, there is a recognized and long felt need for a device which overcomes the aforementioned disadvantages and provides a sensor having a self-contained, long-term energy source with compensation for ambient pressure variations and low sensitivity to temperature changes.

The pressure sensor of the present invention is designed to eliminate many of the previously mentioned problems. Once the pressure sensor is installed by a competent surgeon, the pressure can be read non-invasively by a physician with a minimal amount of special equipment. If an attending physician is not readily available, equipment can be installed in the child's home and the parents instructed in its use.

SUMMARY OF THE INVENTION

The pressure sensor of the present invention is fully implantable and contains a radioactive material so that the pressure can be readout non-invasively. In its preferred form, the sensor system comprises three fluid-filled regions defined by a housing. Non-radioactive fluid is contained in the first region which is in communication with a flexible member placed in the body cavity and exposed to the pressure to be sensed. Non-radioactive fluid is also contained in the third region which is spaced from the first region and closed by a resilient member such as a metallic diaphragm. Radioactive fluid which is immiscible with at least one of the non-radioactive fluids is contained in the second region between the non-radioactive fluids. The interface between the radioactive fluid and one of the non-radioactive fluids is optionally formed by a resilient member such as an elastomeric diaphragm. The housing is located external to the cavity being sensed and preferably situated just under the skin. The pressure acting upon the flexible member causes the fluids, including the radioactive fluid, to move as a function of the pressure sensed. The movement of radioactive fluid within the housing is sensed from outside the skin by a conventional nuclear counter or crystal detector instrument.

The application of the present invention to hydrocephalus greatly facilitates treatment of the defect. The pressure sensor of the present invention when used as an intracranial pressure sensor device has a long life, is fully implantable and does not require any energy source other than the radioactive fluid contained in the device. Two of the major advantages of the present invention are the elimination of implanted energy sources, such as batteries, to operate the device, and the elimination of leads or other penetrations through the skin to provide power or transmit a signal. With a long-lived radioisotope such as promethium 145, the inventive pressure sensing device can be fully implanted and left in place for the life of the patient. Furthermore, the invention contemplates a design and a selection of materials that will assure a negligible radiation dosage to the patient. Although in this application, the invention is primarily intended for a long-term implantation in hydrocephalic children, one may easily appreciate its value in short-term monitoring of head trauma patients.

The inventive pressure monitoring system can be fully implanted with no tubing or wires penetrating the skin, functions accurately to within several millimeters of water pressure and is unaffected by variations in ambient pressure. Also, it is generally insensitive to ambient temperature. Furthermore, the materials used to construct the devices according to the present invention are biologically inert and do not pose any health hazard to the animal or human subject or make the subject more susceptible to mechanical trauma. The sensor unit is of relatively small size and so does not produce unsightly bulging when implanted subdermally.

Other features and advantages of the invention will be apparent from the following description of the preferred embodiments of the invention as shown in the accompanying drawings.

BRIEF DESCRIPTION OF THE DRAWINGS

FIG. 4 is a vertical, cross-sectional view of an another embodiment of the pressure sensor apparatus of the present invention; and FIG. 5 is a horizontal, cross-sectional view of the pressure sensor apparatus of FIG. 4 taken along line 5—5 of FIG. 4.

DESCRIPTION OF THE PREFERRED EMBODIMENTS

Figure 1:
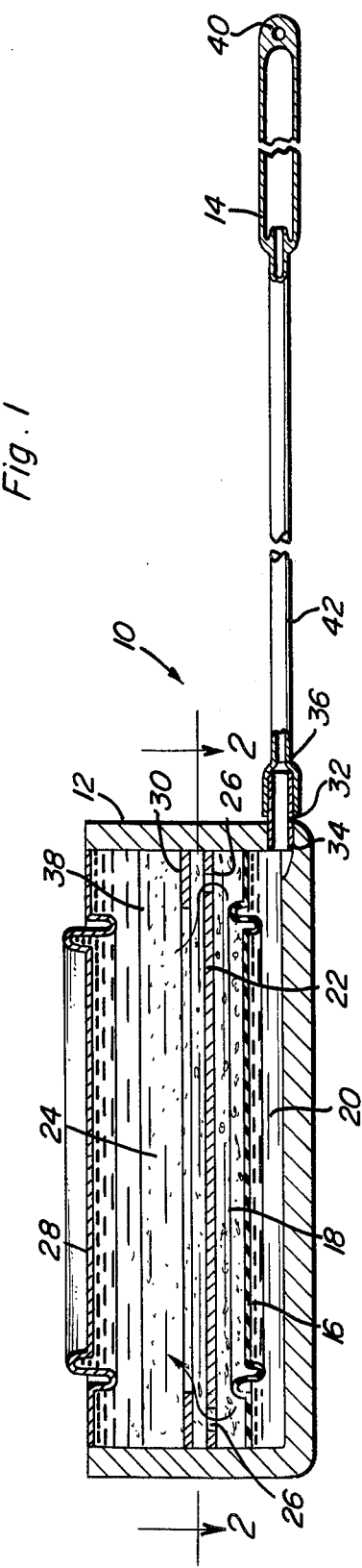
FIG. 1 is a vertical, cross-sectional view of one embodiment of the pressure sensor apparatus of the present invention.

Pressure sensor 10 broadly comprises housing 12 and flexible container or tambour 14. Diaphragm 16 divides the lower portion of housing 12 into upper and lower chambers 18 and 20, respectively. Chamber 18 acts as a reservoir for radioactive fluid and is shielded by shield plate 22.

Figure 2:
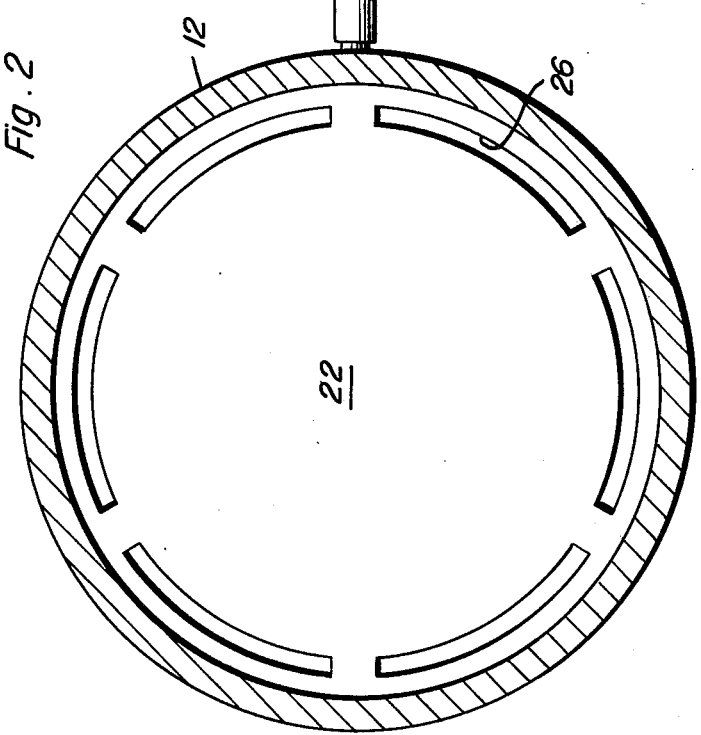
FIG. 2 is a horizontal, cross-sectional view of the pressure sensor apparatus of FIG. 1 taken along line 2—2 of FIG. 1.

Chamber 18 is fluidly connected to chamber 24 in the top portion of housing 12 by means of a plurality of openings 26 extending around the circumference of shield plate 22 as shown in FIG. 2. More specifically, diaphragm 28 and the upper surface of shield plate 22 together form a chamber 24 for receiving radioactive fluid. Openings 26 in shield plate 22 are shielded by ring shield 30 which is annular in shape and is positioned directly above openings 26. Chamber 20 is fluidly connected to tambour 14 by means of tube 32 which fits into port 34 of housing 12 and into opening 36 in the end of tambour 14.

Tambour 14 is filled with a non-radioactive fluid and is placed in the body cavity such as the cranium, bladder, or vena cava of an animal or human for sensing the pressure of the body cavity. Since tambour 14 is normally used in association with the body, the non-radioactive fluid must be inert with respect to the body or, in other words, must be biologically harmless. Furthermore, temperature changes will cause a slight change in the proportion of fluid in tambour 14. Accordingly, it is desirable to use a nonradioactive fluid which has a small volumetric expansion coefficient with temperature. Water is the preferred nonradioactive fluid because of its compatibility with the animal or human body and its small volumetric expansion coefficient of 0.0002 percent degree centigrade. However, any other fluid can be used which meets the above criteria. In particular it is desirable that the fluid have a volumetric change of less than approximately 0.02 percent per degree centigrade which corresponds to a pressure variation of less than one millimeter water per degree centigrade.

Chamber 18 contains sufficient radioactive fluid so that there is always radioactive fluid just filling the openings 26 when the shield plate 22 is held in a level attitude. Chamber 24 also contains a non-radioactive fluid which is immiscible with the radioactive fluid and forms interface 38 therewith. The position of interface 38 in chamber 24 is a function of the quantity of radioactive fluid in chamber 24 and is illustrated in a position in which a positive pressure exists on tambour 14. It will be readily apparent that diaphragm 16 can also be omitted if the non-radioactive fluid in tambour 14 and chamber 20 is one which is immiscible with the radioactive fluid. Moreover, diaphragm 16 can be omitted and a diaphragm placed at the interface 38 in which case the non-radioactive fluid in chamber 24 does not have to be immiscible with the radioactive fluid. The preferred immiscible, non-radioactive fluid is silicone fluid.

Figure 3:
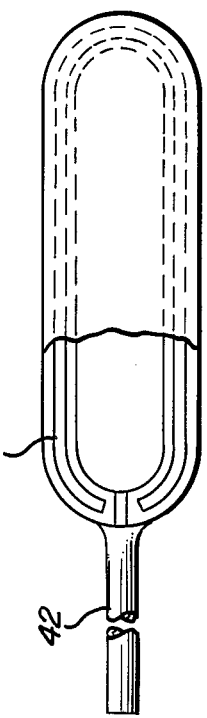
FIG. 3 is a plane view, partly in section, of the flexible tambour shown in FIG. 1.

Tambour 14 must be constructed of a flexible material so that it will be responsive to pressure changes and a material which is impermeable to the non-radioactive fluid and in particular to water. A desirable material from the standpoint of flexibility and tissue compatibility is silicone rubber such as the elastomer sold under the trademark Silastic. However, extensive experimentation has shown that silicone rubber tambours cannot be used because of loss of fluid through the wall of the tambour. It was recently discovered that butyl rubber which has a low diffusion coefficient for water is a suitable material from which the tambour can be fabricated. This discovery is disclosed and claimed in the commonly assigned application cross-referenced above. The butyl rubber tambour can be coated with a thin coating of silicone rubber if desired to provide better tissue compatibility. Tambour 14 is essentially a flexible container or sack which can be formed in any suitable shape such as cylindrical, disc-shaped, spheroidal or planar. As shown in FIG. 3, wire 40 can be placed in tambour 14 to give it suitable shape. Furthermore, a coiled spring (not shown) can be placed in neck portion 42 of tambour 14.

Sensor 10 is constructed so that it is only responsive to pressure changes in the body cavity being sensed and is not responsive to ambient pressure changes which are exerted equally on both flexible tambour 14 and diaphragm 28. In the embodiment shown in FIG. 1, diaphragm 28 is adapted to be directly exposed to ambient pressure.

Housing 12 is preferably constructed of titanium. Diaphragm 16 shown in the embodiment of FIG. 1 is preferably constructed of a water impermeable elastomer such as butyl rubber or any other elastomer which is impermeable to the fluid in tambour 14. In the case of butyl rubber, it may be desirable to use a leaf spring in conjunction therewith to prevent cold flow. Diaphragm 28 is preferably a metallic diaphragm formed from titanium. Tubing 32 is also preferably constructed of titanium. Shield plate 22 and ring shield 30 preferably comprise tantalum shielding; however, tungsten, iridium, rhenium, platinum, rhodium, gold, niobium, or other suitable heavy metals can be used. Wire 40 in tambour 14 is preferably constructed of tantalum. All tubing, housing and diaphragm joints are suitably formed by brazing or the use of suitable gaskets, etc. Finally, the entire sensor can be coated with a thin coating of silicone rubber or placed in a silicone rubber boot if desired to provide better tissue compatibility.

When readings are taken with a detector such as a nuclear counter or crystal detector instrument, the patient is restrained in such a manner that the sensor housing 12 is maintained in the level attitude. Changes in pressure of the body cavity being monitored compress tambour 14 and cause fluid to flow from tambour 14 through tubing 32 and into chamber 20 in housing 12. Tambour 14 offers effectively no resistance to the pressure changes because of its flexible construction.

Housing 12 provides a mechanical interface between the non-radioactive, pressure sensing fluid and the radioisotope bearing fluid. Diaphragm 16 separates the two fluids and provides part of the force necessary to balance the body cavity pressure. As diaphragm 16 deflects under increasing body cavity pressure, it forces radioactive fluid out of the radioactive fluid reservoir formed by chamber 18, through openings 26 and into chamber 24. This causes interface 38 and the non-radioactive fluid to move and forces diaphragm 28 to deflect, also adding to the force exerted to balance the body cavity pressure. As the pressure of the body cavity increases, more fluid enters housing 12. Since the amount of fluid in the sensor reservoir formed between shield plate 22 and the bottom surface of diaphragm 28 is a function of the body cavity pressure, and the count rate is directly dependent on the fluid quantity, the body cavity pressure can immediately be determined via the count rate.

FIGS. 4 and 5 show another embodiment of the pressure sensor of the present invention. In this embodiment, the storage and sensor reservoirs of pressure sensor 100 are also placed in the same housing 102. Diaphragm 104 separates chamber 106 in housing 102 from chamber 108. Chamber 108 is filled with radioactive fluid and is equivalent to storage reservoir chamber 18 in FIG. 1. Chamber 108 is connected by passage 110 to chamber 112. Chamber 112 is equivalent to the sensor reservoir formed between shield plate 22 and the lower surface of diaphragm 28 in FIG. 1. Chamber 112 includes enlarged inlet portion 114 and spiral portion 116 which is of reduced cross-sectional area. Chamber 112 is closed by pressure compensating end portion 118 which is resilient and equivalent to diaphragm 28 in FIG. 1. Spiral portion 116 is preferably constructed of a capillary tube and pressure compensating end portion 118 which contains a non-radioactive fluid immiscible with the radioactive fluid from a suitable elastomer such as silicone or butyl rubber.

Attached to housing 102 by tube 120 is tambour 122. Tambour 122 is the same as tambour 14 in FIG. 1. In this embodiment, tambour 122 is placed in contact with the body cavity to be sensed and changes in pressure in the body cavity cause non-radioactive fluid to pass through tube 120 and into chamber 106 where diaphragm 104 deflects and forces radioactive fluid out of chamber 108, through passage 110 and into chamber 112. As in FIG. 1, at least the portion 124 of housing 102 must be formed from a shielding material such as tantalum so that only changes in the quantity of radioactive fluid in chamber 112 are detected by the radioactivity sensor through mask 126 which has a spiral opening 128 corresponding in shape to spiral portion 116 of chamber 112.

Because of the unique construction of pressure sensors 10 and 100, no external leads are required and the sensor occupies very little space under the scalp so that it produces only a slight elevation thereof when the sensor is used for sensing intracranial pressure. Tambour 14, for example, can be placed through a burr hole within a cerebral ventrical and housing 12 positioned outside the skull, but implanted under the scalp. A change in the volume of non-radioactive fluid in chamber 24 is detected by measuring the change in radioactivity immediately adjacent to the skin. Thus, the skin does not have to be penetrated to obtain reliable pressure information. The quantity of the radioisotope utilized in the device is extremely small, typically less than one microcurie and results in surface dose rates to the scalp and skull which are on the order of 100 times less than the rates necessary to cause detectable changes in the most radiosensitive body tissue and thus will not adversely affect the adjacent skin or bone marrow.

The radioisotope used in the present invention should have a half life which is sufficiently long to give acceptable end-of-life pressure data. The radioisotope should also be safe as a source of radiation when used immediately beneath the scalp or within a body cavity so that no damage will occur if it is inadvertently released into the body. Another requirement is that the radioisotope must be detected efficiently which means that it must have a high skin transmissibility as well as a high detector efficiency. In addition, the radioisotope must be chemically compatible with and must remain in solution within the radioactive fluid chambers and must be insoluble in the non-radioactive fluid.

The preferred radioisotope used in the present invention is promethium 145. Promethium has an 18 year half life and a soft gamma emission which can be easily transmitted through the skin and efficiently detected while being safely used in quantities necessary for statistical counting accuracy. Among other radioisotopes which can be used in the invention is holmium 163 which has a 40 to 60 year half life. The radioisotope is preferably used in solution in hydrochloric acid which is immiscible with the preferred non-radioactive fluid, namely, silicone fluid.

While the pressure sensor of the present invention has been illustrated primarily as an intracranial pressure sensor, it should be understood that the sensor is also useful in other body cavities in the treatment or care of animals and humans. Thus, valuable information may be derived from monitoring pressure in the vena cava, bladder, or some other body cavity, the foregoing details with respect to intracranial pressure being but a specific illustration of the application of the present invention to a particular problem and, in that sense, illustrative rather than limiting. Furthermore, while the preferred embodiments of the invention have been disclosed, it should be understood that the invention is not limited to such embodiments but only as defined in the appended claims.

What is claimed is:

1. A pressure sensor apparatus comprising a housing having first and second regions, a first non-radioactive fluid contained within said first region and a second non-radioactive fluid contained with said second region, a radioactive fluid contained within said housing between said first and second non-radioactive fluids, said radioactive fluid being immiscible with at least one of said first and second non-radioactive fluids, radiation shielding means associated with said housing for shielding a portion of said radioactive fluid, pressure communication means impermeable to said non-radioactive fluid in communication with said first region so that pressure acting upon said pressure communication means will cause said radioactive fluid to move, and resilient means closing said second region of said housing for permitting movement of said radioactive fluid, said radioactive fluid being moved in said housing as a function of the pressure acting upon said pressure communication means whereby said portion of radioactive fluid shielded by said shielding means varies as a function of said pressure.

2. The apparatus of claim 1 and further comprising second resilient means separating said first non-radioactive fluid from said radioactive fluid.

3. The apparatus of claim 1 in which at least a portion of said housing which acts to confine said radioactive fluid is of smaller cross-section than the portion of said housing which confines said first and second non-radioactive fluids.

4. The apparatus of claim 1 in which at least a portion of said housing which confines said radioactive fluid is a capillary tube.

5. The apparatus of claim 1 in which at least a portion of said housing which confines said radioactive fluid is spiral in shape.

6. The apparatus of claim 1 in which said resilient means comprises a metallic diaphragm.

7. The apparatus of claim 1 in which said first and second non-radioactive fluids are silicone fluid and said radioactive fluid comprises promethium 145 in solution in hydrochloric acid.

8. The apparatus of claim 1 in which said resilient means is adapted to be exposed to the atmosphere so that said apparatus is insensitive to changes in ambient pressure.

9. An intracranial pressure sensor apparatus of the type to be positioned between the scalp and skull and having a pressure transferring mechanism extending through the skull into the intracranial cavity comprising a transfer housing adapted to be positioned between the skull and scalp, said housing having first and second ends, said housing having inlet means connected to said first end, pressure sensing means connected at one end to said inlet means and having its other end adapted to be positioned inside the skull, a first nonradioactive fluid contained within said pressure sensing means and said first end of said housing, said pressure sensing means being flexible and impermeable to said non-radioactive fluid, a second non-radioactive fluid contained within said second end of said housing, first resilient means closing said second end of said housing, radioactive fluid contained within said housing between said first and second non-radioactive fluids and being immiscible with said second non-radioactive fluid, radiation shielding means associated with said housing for shielding a portion of said radioactive fluid, so that pressure acting upon said pressure sensing means within the skull will cause said radioactive fluid to be transferred within said housing and said portion of radioactive fluid shielded by said shielding means will vary whereby the unshielded radioactive fluid can be sensed externally of the scalp by a radioactive detector.

* * * * *